(12) United States Patent
Rao et al.

(10) Patent No.: US 7,285,571 B2
(45) Date of Patent: *Oct. 23, 2007

(54) HERBAL CHEMICAL COMPOSITION FOR THE TREATMENT OF CANCER

(75) Inventors: Janaswamy Madhusudana Rao, Hyderabad (IN); Pullela Venkata Srinivas, Hyderabad (IN); Jhillu Singh Yadav, Hyderabad (IN); Kondapuram Vijaya Raghavan, Hyderabad (IN); Ajit Kumar Saxena, Jammu (IN); Mutiah Shanmugavel, Jammu (IN); Himani Kampasi, Jammu (IN); Gulam Nabi Qazi, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 279 days.

This patent is subject to a terminal disclaimer.

(21) Appl. No.: 10/463,060

(22) Filed: Jun. 17, 2003

(65) Prior Publication Data
US 2003/0216464 A1 Nov. 20, 2003

Related U.S. Application Data

(62) Division of application No. 10/013,133, filed on Dec. 7, 2001, now Pat. No. 6,649,650.

(51) Int. Cl.
*A61K 31/34* (2006.01)
*A61K 31/37* (2006.01)

(52) U.S. Cl. .................. 514/468; 424/725; 514/461; 514/473

(58) Field of Classification Search ............... 514/461, 514/468, 473; 424/725
See application file for complete search history.

(56) References Cited

U.S. PATENT DOCUMENTS

| 6,271,257 B1 * | 8/2001 | Mutanen .............. 514/461 |
| 6,458,831 B1 | 10/2002 | Rao et al. |
| 6,537,593 B2 | 3/2003 | Rao et al. |
| 6,649,650 B2 * | 11/2003 | Rao et al. ............. 514/461 |

OTHER PUBLICATIONS

Ingram et al "Case-control study of phyto-oestrogens and breast cancer" The Lancet vol. 350 Iss 9083 Oct. 4, 1997 pp. 990-994.*
Watanabe et al Abs of "Intake of phytoestrogen and prevention of cancer" AN 1997:369167 CAPLUS DN 127:80731.*

* cited by examiner

*Primary Examiner*—Herbert J. Lilling
(74) *Attorney, Agent, or Firm*—Merchant & Gould P.C.

(57) ABSTRACT

The present invention relate to a novel synergistic composition of lignans exhibiting anticancer activities for breast, cervix, neuroblastoma, colon, liver, lung, mouth, ovary and prostate cancer obtained from the plant extract of *Cedrus deodra*, said composition comprising of (–)-Matairesinol in the range of 9 to 13% by weight, (–)-Wikstromol in the range of 75 to 79% by weight, Dibenzylbutyrolactol in the range of 7 to 11% by weight, and Unidentified material in the range of 2.6 to 3% by weight; further, the synergistic composition of lignan is used in combination with pharmaceutically acceptable carriers for inhibiting growth of various human cancer cell lines selected from breast, cervix, neuroblastoma, colon, liver, lung, mouth, ovary and prostate tissues.

17 Claims, 1 Drawing Sheet

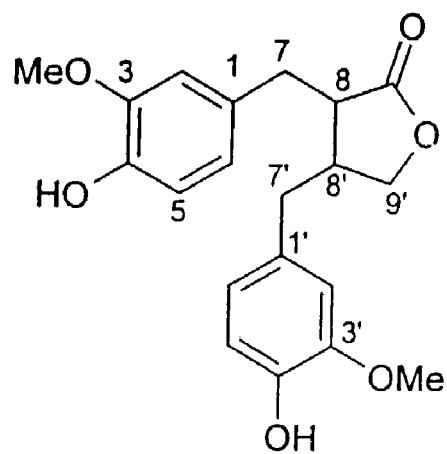
(−)-Matairesinol (1)
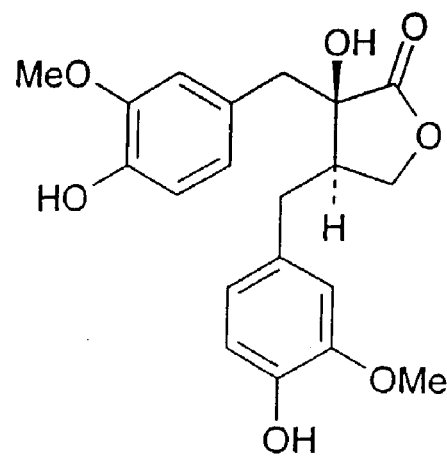
(−)-Wikstromol (2)
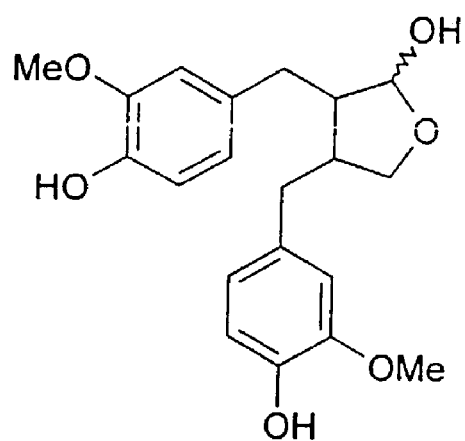
Dibenzylbutyrolactollignan (3)

HERBAL CHEMICAL COMPOSITION FOR THE TREATMENT OF CANCER

FIELD OF INVENTION

The present invention relates to a novel herbal composition for the treatment of cancer. The present invention particularly relates to an herbal formulation comprising mixture of lignans isolated from the plant *Cedrus Deodara*.

BACKGROUND OF INVENTION

Cancer or neoplasm is the malignant new growth anywhere and elsewhere in the body system. It is characterized by unregulated proliferation of cells and a growing public health problem whose estimated worldwide new incidence is about six million cases per year. In most of the countries, cancer is second only to heart disease as cause of death. It can arise in any organ of the body but some sites are prone to attack than others such as breast, throat, intestine, leukocytes etc. Each cancer is propagated from a single cell that cut at some stage, it becomes free from its territorial restraints, which form a family of cells that multiply without limits and appear in the form of tumors.

During the transition from normal cell to a tumor cell a profound and heritable change occurs which allows a tumor cell to determine its own activities largely irrespective of the laws that govern so precisely the growth of all normal cells in an organism. This newly acquired property, which is known as autonomy, is the most important single characteristic of tumor cells since without it there would be no tumors. Another distinguishing characteristic of tumor cells is their lack of perfect form of function. The differences that exist between cancer and normal cells are that, compared to normal cells, cancer cells have a) low pH b) greater free radical character c) tumor produced hormone peptides d) tumor associated antigens e) lower calcium ion and higher potassium ion concentration f) different potassium isotope ratios g) elevated amounts of methylated nucleotides h) higher concentrations of plasma microproteins and mucopolysacharides i) greater need of exogenous zinc and j) high biowater content.

Many of the gross causes of cancer, such as dietary, environmental, occupational exposure to certain chemical substances or forms of electromagnetic radiation, have been elucidated through epidemiological studies. It is imperative, therefore, that they be identified and eliminated from the environment in so far as that is possible in modem industrial societies. In the annals of therapy, a quest to conquer, the impasse of cancer has been always fascinated by and large all disciplines of scientific community, especially natural product chemists. In 19$^{th}$ and 20$^{th}$ century, lot of research work has been carried out to find out the driving force behind this dreadful disease as well as large number of drugs have been introduced to counter its menace.

It is worthwhile at this juncture to look briefly at a few most powerful chemotherapeutic agents, which have been of paramount importance to the mankind and also to the researchers who have been actively involved in the synthesis and isolation of anticancer drugs. Lignans have been isolated from a number of plants (Achenbach, H., Waibel, R. and Meusah, I. *Phytochemistry*, 22 (3), 749-753 (1983); Nishibe, S., Hisada, S. and Inagaki, I. *Phytochemistry*, 10, 2231-2232 (1971); Barrero, A. F., Haidour, A. and Dorado, M. M. *J. Nat. Prod.* 42,159-162(1979)).

Recent studies on the biological activities of lignans prove beyond doubt the efficacy of these phytochemicals as cytotoxic agents (Macrae, W. D. and Towers, G. H. N. *Phytochemistry* 23 (6), 1207-1220 (1984)). Also recently lignans have been isolated from human urine and blood. This fact also suggests that lignans are playing a definite role in human physiology.

With the above background, the applicants have focussed their attention towards the identification and isolation of potent cytotoxic agents from plants. Literature data suggests the presence secoisolariciresinol in *Cedrus deodara* (Agarwal, P. K. and Rastogi, R. P. *Phytochemistry*, 21 (6), 1459-1461 (1982)) which is in all likelihood may be an artefact, is a proven antioxidant. Further investigation on *Cedrus Deodara* carried out by us led us to the isolation of a new lignan mixture comprising essentially (−)-Matairesinol, (−)-Wikshtronol and Dibenzyl butyrolactol in an extremely significant yield, *Cedrus deodara* is also a new source for these lignans. (−)-Wikstromol was first reported from *wikstroemia viridiflora* (Nishibe, S., Hisada, S. and Inagaki, I. *Phytochemistry*, 10, 2231-2232 (1971)). Matairesinol was isolated from a number of sources before (Nishibe, S., Hisada, S. and Inagaki, I. *Phytochemistry*, 10, 2231-2232 (1971); Tandon, S. and Rastogi, R. P. *Phytochemistry*, 15, 1789-1791 (1976)). The isolation of the dibenzylbutyrolactol [4,4',9-trihydroxy-3,3'-dimethoxy-9,9'-epoxy lignan] was reported only once previously from the wood of *Abies pinsapo* (Barrero, A. F., Haidour, A. and Dorado, M. M. *J. Nat. Prod.* 42, 159-162 (1979)).

Keeping in mind the high yields of the lignans from *Cedrus deodara* and also the excellent biological activities and lignans in general (Macrae, W. D. and Towers, G. H. N. *Phytochemistry* 23(6), 1207-1220 (1984).

OBJECTS OF THE INVENTION

Main object of the invention relates to herbal compositions for the treatment of human cancer cells.

Another object of the invention relates to herbal compositions for the treatment of human cancer cells obtained from a plant source.

Another object of the invention relates to in-vitro cytotoxicity of lignan mixtures isolated from *Cedrus deodara* against various human cancer cell lines.

Still another object of the invention relates to cytotoxicity of individual lignans isolated from *Cedrus deodara* against various human cancer cell lines.

Still another embodiment of the invention relates to a method of isolation of the active lignan mixture from the plant source namely *Cedrus deodara*.

Yet another object of the invention relates to a synergistic lignan composition obtained from plant *cedrus deodara* for inhibiting the growth of human cancer cells. Yet another object of the invention relates to a composition comprising individual lignans isolated from plant *cedrus deodara* for inhibiting the growth of human cancer cells.

Yet another embodiment relates to method of treating mammals, particularly human beings affected by cancer.

SUMMARY OF THE INVENTION

Accordingly, the present invention provides a novel synergistic composition of lignans exhibiting anticancer activities for breast, cervix, neuroblastoma, colon, liver, lung, mouth, ovary and prostate cancer obtained from the plant extract of *Cedrus deodra*, said composition comprising of (a) (−)-Matairesinol in the range of 9 to 13% by weight, (b) (−)-Wikstromol in the range of 75 to 79% by weight, (c) Dibenzylbutyrolactol in the range of 7 to 11% by weight, and
(d) Unidentified material in the range of 2.6 to 3% by weight, Further, the synergistic composition of lignan may be used in combination with pharmaceutically acceptable carriers for inhibiting various human cancer cell lines.

DETAILED DESCRIPTION OF THE INVENTION

An attempt is made to establish anticancer activity to the lignan mixture isolated from *Cedrus deodara*. The individual constituents isolated from the chloroform extract of *Cedrus deodara* wood have shown lesser level of activity compared to the lignan mixture establishing the principle of synergy.

Accordingly, the present invention provides a novel synergistic composition of lignans exhibiting anticancer activities for breast, cervix, neuroblastoma, colon, liver, lung, mouth, ovary and prostate cancer obtained from the plant extract of *Cedrus deodra*, said composition comprising of (e) (−)-Matairesinol in the range of 9 to 13% by weight,
(f) (−)-Wikstromol in the range of 75 to 79% by weight,
(g) Dibenzylbutyrolactol in the range of 7 to 11% by weight, and
(h) Unidentified material in the range of 2.6 to 3% by weight, In another embodiment, wherein the synergistic lignans composition inhibits the growth of cancer cells of breast up to 80% at a concentration ranging from 30-100 μg/ml.

Still another embodiment, the breast cell line is selected from group consisting of MCF-7 and T-47-D.

Yet another embodiment, wherein the synergistic lignans composition inhibits the growth of cancer cells of cervix up to 89% at a concentration ranging from 30-100 μg/ml. Yet another embodiment, the cervix cell line is selected from the group consisting of Hela and SiHa.

Yet another embodiment, wherein the synergistic lignans composition inhibits the growth of cancer cells of neuroblastoma up to 96% at a concentration ranging from 30-100 μg/ml.

Yet another embodiment, wherein cancer cell line of neuroblastoma is selected from the group consisting of SF-539, SKNMC, IMR-32, SKNSH and SNB-78.

Yet another embodiment, wherein the synergistic lignan composition inhibits the growth of cancer cells of colon up to 97% at a concentration ranging from 30-100 μg/ml.

Yet another embodiment, wherein cancer cell line of colon is selected from the group consisting of Colo-205, HCT-15, HT-29 and SW-620.

Yet another embodiment, wherein the synergistic lignan composition inhibits the growth of cancer cells of liver up to 73% at a concentration ranging from 30-100 μg/ml.

Yet another embodiment, wherein the cancer cell line of liver is selected from the group consisting of Hep-2 and Hep-G-2.

Yet another embodiment, wherein the synergistic lignan composition inhibits the growth of cancer cells of lung up to 83% at a concentration ranging from 30-100 μg/ml.

Yet another embodiment, wherein the cancer cell line of lung is selected from the group consisting of A-549, NC1-H23 and HOP-18.

Yet another embodiment, wherein the synergistic lignan composition inhibits the growth of cancer cells of mouth up to 100% at a concentration ranging from 30-100 μg/ml.

Yet another embodiment, wherein the cancer cell line of mouth is KB.

Yet another embodiment, the synergistic lignan composition inhibits the growth of cancer cells of ovary up to 96% at a concentration ranging from 30-100 μg/ml.

Yet another embodiment, wherein the cancer cell line of ovary is selected from the group consisting of OVCAR-5, NIH-OVCAR-3 and SK-OV-3.

Yet another embodiment, wherein the synergistic lignan composition inhibits the growth of cancer cells of prostrate up to 98% at a concentration of ranging from 30-100 μg/ml.

Yet another embodiment, wherein the cancer cells line of prostrate tissue is selected from the group consisting of DU-145 and PC-3.

Yet another embodiment, wherein the synergistic composition of lignan is administered to the patient in combination with a pharmaceutically acceptable additive, carrier, diluent, solvent, filter, lubricant, excipient, binder, or stabilizer.

Yet another embodiment, wherein synergistic lignan composition can be administered systemically and/or orally or any other suitable method.

Yet another embodiment, wherein the subjects are selected from animals or mammals preferably humans.

One more embodiment of the invention relates to a composition exhibiting anti cancer activities for cancer cell lines selected mainly from the group consisting breast, cervix, neuroblastoma, colon, liver and lung, said composition comprising pharmaceutically effective dosage of (−)-wikstromol or a formulation containing.(−)-wikstromol.

Another embodiment of the invention, wherein the cancer cell line used are selected from group consisting breast cells MCF-7 and ZR-75-1; cervix cell SiHa; neuroblastoma cells SKNMC and IMR-32; colon cells colo-205HT-29 and SW-620; liver cell Hep-2; and lung cell A-549.

Still another embodiment of the invention, wherein above said composition inhibits the growth of cancer cells of breast up to 51% at a concentration of about 100 μg/ml.

Yet another embodiment of the invention, wherein said composition inhibits the growth of cancer cells of cervix up to 37% at a concentration of about 100 μg/ml.

Yet another embodiment of the invention, wherein said composition inhibits the growth of cancer cells of neuroblastoma up to 56% at a concentration of about 100 μg/ml.

Yet another embodiment of the invention, wherein said composition inhibits the growth of cancer cells of colon up to 67% at a concentration of about 100 μg/ml.

Yet another embodiment of the invention, wherein said composition inhibits the growth of cancer cells of liver up to 46% at a concentration of about 100 μg/ml.

Yet another embodiment of the invention, wherein said composition inhibits the growth of cancer cells of lung up to 56% at a concentration of about 100 μg/ml.

Yet another embodiment of the invention, wherein said composition inhibits is administered in combination with a pharmaceutically acceptable carriers, additives, diluents, solvents, filters, lubricants, excipients, binders and stabilizers.

Yet another embodiment, said composition can be administered systematically and/or orally or any other suitable method.

Yet another embodiment, wherein the subjects are selected from animals or mammals preferably humans.

One more embodiment of the present invention provides a composition exhibiting anti cancer activities for cancer cell lines selected mainly from the group consisting breast, cervix, neuroblastoma, colon, liver and lung, said composition comprising a pharmaceutically effective dosage of (−)-Matairesinol or a formulation containing (−)-Matairesinol.

Yet another embodiment, wherein the cancer cell lines used are selected from the group comprising of breast cells MCF-7 and ZR-75-1; cervix cell SiHa; neuroblastoma cells SKNMC and IMR-32; colon cells Colo-205, HT-29 and SW-620; liver cell Hep-2; and lung cell A-549.

Yet another embodiment, wherein composition containing (−)-Matairesinol inhibits the growth of cancer cells of breast up to 62% at a concentration of about 100 μg/ml Yet another embodiment, wherein above said composition inhibits the growth of cancer cells of cervix up to 63% at a concentration of about 100 μg/ml Yet another embodiment, wherein above said composition inhibits the growth of cancer cells of neuroblastoma up to 77% at a concentration of about 100 μg/ml Yet another embodiment, wherein above said composition inhibits the growth of cancer cells of colon up to 93% at a concentration of about 100 μg/ml Yet another embodiment, wherein above said composition inhibits the growth of cancer cells of liver up to 64% at a concentration of about 100 μg/ml Yet another embodiment, wherein above said composition inhibits the growth of cancer cells of lung up to 65% at a concentration of about 100 μg/ml Yet another embodiment, wherein above said composition is administered to the patient in combination with a pharmaceutically acceptable carriers additives, diluents, solvents, filters, lubricants, excipients, binders and stabilizers.

Yet another embodiment, wherein above said composition may be administered systematically or orally.

Yet another embodiment, wherein the subjects are selected from animals or mammals preferably humans One more embodiment of the invention relates to a process for isolation of synergistic lignan composition from the plant extract of *Cedrus deodra* comprises steps of:
  (a) powdering the plant *Cedrus deodra*,
  (b) extracting the powdered plant in a soxhlet apparatus successively with hydrocarbon solvent followed by halogenated solvent,
  (c) concentrating the extract of hydrocarbon solvent and halgenated solvent separately, and
  (d) purifying halogenated solvent extract by chromatography on an adsorbent by eluting with mixture of organic solvents to yield (−)-Matairesinol 1 to 2% by weight, (−)-Wikstromol 10 to 14% by weight, Dibenzylbutyrolactol 1 to 2% by weight and unidentified material 0.2 to 0.3% by weight with respect to extract and which together constitute as synergistic lignan composition.

Another embodiment of the invention, in step (a) wherein the plant part is wood and in step (b) the hydrocarbon solvent is selected from group of hexane and petroleum ether, preferably hexane.

Still another embodiment of the invention, the halogenated solvent is selected from carbon tetrachloride, methylene chloride or chloroform, preferably chloroform.

Still another embodiment of the invention, in step (c) the extracts are concentrated under vacuum and the purification is carried out using silica gel as an adsorbent and eluting with different proportions of chloroform-methanol mixture to get pure compounds (.)-wikstromol, (−)-metairesinol, dibenzylbutyrolactol, an unidentified material and which together constitute as synergistic lignan composition.

One more embodiment of the invention provide a method of treating a patient with cancer mainly breast, cervix, neuroblastoma, colon, liver, lung, mouth, ovary and prostate, said method comprising administering a pharmaceutically effective dosage of synergistic composition of lignan composition to the patient.

In another embodiment of the invention, wherein the said synergistic lignan composition is used in combination with pharmaceutically acceptable carriers.

Still another embodiment of the invention, wherein synergistic lignan composition may be administered systemically and/or orally or any other suitable method. Still another embodiment of the invention, wherein the subjects are selected from animals or mammals preferably humans.

Yet another embodiment of the invention, wherein said synergistic lignan composition inhibits the growth of cancel cells of breast up to 80% at a concentration ranging from 30-100 μg/ml.

Yet another embodiment of the invention, breast cell lines inhibited are MCF-7 and T-47-D.

Yet another embodiment of the invention, wherein synergistic lignan composition inhibits the growth of cancel cells of cervix up to 81% at a concentration ranging from 30-100 μg/ml.

Yet another embodiment of the invention, cervix cell lines inhibited are Hela and SiHa.

Yet another embodiment of the invention, wherein synergistic lignan composition inhibits the growth of cancel cells of neuroblastoma up to 92% at a concentration ranging from 30-100 μg/ml.

Yet another embodiment of the invention, wherein neuroblastoma cell lines inhibited are SF-539, SKNMC, IMR-32, SKNSH and SNB-78.

Yet another embodiment of the invention, wherein synergistic lignan composition inhibits the growth of cancel cells of colon up to 95% at a concentration ranging from 30-100 μg/ml.

Yet another embodiments of the invention, wherein colon cell lines inhibited are Colo-205, HCT-15, HT-29 and SW-620.

Yet another embodiment of the invention, wherein synergistic lignan composition inhibits the growth of cancel cells of liver up to 73% at a concentration ranging from 30-100 μg/ml.

Yet another embodiment of the invention, wherein liver cell line inhibited is Hep-2.

Yet another embodiment of the invention, wherein synergistic lignan composition inhibits the growth of cancel cells of lung up to 92% at a concentration ranging from 30-100 μg/ml.

Yet another embodiment of the invention, wherein lung cell lines inhibited are A-549 and NC1-H23.

Yet another embodiment of the invention, wherein synergistic lignan composition inhibits the growth of cancel cells of mouth up to 99% at a concentration ranging from 30-100 μg/ml.

Yet another embodiment of the invention, wherein mouth cell line inhibited is KB Yet another embodiment of the invention, wherein synergistic lignan composition inhibits the growth of cancel cells of ovary up to 96% at a concentration ranging from 30-100 μg/ml.

Yet another embodiment of the invention, wherein ovary cell lines inhibited are OVCAR5 and SK-OV-3.

Yet another embodiment of the invention, wherein synergistic lignan composition inhibits the growth of cancel cells of prostrate up to 98% at a concentration ranging from 30-100 μg/ml Yet another embodiment of the invention, wherein prostrate cell lines inhibited are DU-145 and PC-3.

Yet another embodiment of the invention, wherein synergistic lignan composition is administered to the patient in combination with a pharmaceutically acceptable additive, carrier, diluent, solvent, filter, lubricant, excipient, binder, or stabilizer.

Yet another embodiment of the invention, wherein amount of synergistic composition administered is ranging from 10 to 500 mg/kg body weight for at least one dose per day.

Yet another embodiment of the invention, wherein, amount of synergistic composition administered is preferably ranging from 50 to 350 mg/kg body weight.

Another more embodiment of the invention relates to a method of treating a patient with cancer mainly breast, cervix, neuroblastoma, colon, liver, lung, mouth, ovary and prostate, said method comprising administering a pharmaceutically effective dosage of (−)-wikstromol or a composition containing (−)-woikstromol. to the patient.

Still another embodiment, wherein the said composition inhibits the growth of cancer cells consisting of breast cells, cervix cells, neuroblastoma cells, colon cells, liver cell and lung cell up to 51%, 37%, 56%, 67%, 46% and 56% respectively.

Still another embodiment, wherein the cancer cell lines are selected from the group comprising of breast cells MCF-7 and ZR-75-1; cervix cell SiHa; neuroblastoma cells SKNMC and IMR-32; colon cells Colo-205, HT-29 and SW-620; liver cell Hep-2; and lung cell A-549.

Yet another embodiment, wherein the composition is used singly or in combination with pharmaceutically acceptable carriers.

Yet another embodiment, wherein the composition can be administered systematically and/or orally or any other suitable method.

Yet another embodiment, wherein the subjects are selected from animals or mammals preferably humans.

Yet another embodiment, wherein the amount of composition administered is ranging from 10 to 500 mg/kg body weight at least once in a day.

Yet another embodiment, wherein the amount of composition administered is preferably ranging from 75 to 300 mg/kg body weight at least once in a day.

Yet another embodiment, wherein the (−)-wikstromol is administered to the patient in combination with a pharmaceutically acceptable carriers additives, diluents, solvents, filters, lubricants, excipients, binders and stabilizers.

One more embodiment relates to a method of treating a patient with cancer mainly breast, cervix, neuroblastoma, colon, liver and lung, said method comprising administering a pharmaceutically effective dosage of (−)-Matairesinol or a composition containing (−)-Matairesinol to the patient.

Another embodiment of the invention, wherein the said composition inhibits the growth of cancer cells consisting of breast cells, cervix cells, neuroblastoma cells, colon cells, liver cell and lung cell up to 62%, 63%, 77%, 93%, 64% and 65% respectively.

Yet another embodiment, wherein the cancer cell lines are selected from the group comprising of breast cells MCF-7 and ZR-75-1; cervix cell SiHa; neuroblastoma cells SKNMC and IMR-32; colon cells Colo-205, HT-29 and SW-620; liver cell Hep-2; and lung cell A-549.

Yet another embodiment, the said composition is used singly or in combination with pharmaceutically acceptable carriers.

Yet another embodiment the said composition may be administered systematically or orally.

Yet another embodiment, wherein the subjects are selected from animals or mammals preferably humans.

Yet another embodiment, the amount of composition administered is ranging from 10 to 500 mg/kg body weight at least once in a day.

Yet another embodiment, the amount of composition administered is preferably ranging from 75 to 300 mg/kg body weight at least once in a day.

Yet another embodiment, the said composition is administered to the patient in combination with a pharmaceutically acceptable carriers additives, diluents, solvents, filters, lubricants, excipients, binders and stabilisers.

The present invention embodies isolation of new cytotoxic mixture from an entirely new source. The lignan mixture, in vitro, significantly inhibited the growth of number of human cancer cell lines (breast: MCF-7 & T-47-D, cervix: Hela & SiHa, neuroblastoma: SF-539, SKNMC, IMR-32, SKNSH & SNB-78, colon: Colo-205, HCT-15, HT-29 & SW-620, liver: Hep-2, lung: A-549 & NC1-H23, mouth: KB, ovary: OVCAR5 & SK-OV-3 and prostate: DU-145 & PC-3) representing different organs.

The present invention relates to a synergistic composition comprising (−)-Matairesinol, (−)-Wikstromol, Dibenzylbutyrolactol and unidentified material providing a unexpected results of showing enhanced cytotoxicity against cancer cell lines, which is substantiated by remarkable cytotoxicity results against cancer cell lines selected from Breast, Cervix, Neuroblastoma, Colon, Liver, Lung, Oral, Ovary and Prostate tissues. In fact, the compositions is synergistic because the activity is remarkable and such surprisingly enhanced activity of the composition cannot be expected from the mere aggregation of the properties of the individual ingredients.

In other words, the composition does not possess the mere addition of the properties of its ingredients, but an enhanced activity, which further substantiates the efficacy of the synergistic composition isolated. Further, the amounts of the ingredients also impart/contribute for the enhanced activity of the composition.

The following examples are given by way of illustration and therefore should not be construed to limit the scope of the present invention.

BRIEF DESCRIPTION OF THE ACCOMPANYING DRAWINGS

FIG. 1 represents the structural formulae of (−)-Matairesinol [1]; (−)-wikstromol [2] and Dibenzylbutyrolactol [3].

EXAMPLE-1

Isolation and Identification of Individual Constituents:

The dried wood pieces of *Cedrus Deodara* was powdered and loaded (200 g) in a soxilet apparatus. The powder was first extracted with hexane and followed by chloroform. The chloroform extract was concentrated under vacuum and the residue was loaded on a silica gel column (60-120 mesh, for 10 g, residue, 3.5 cm dia. Column loaded to a length of 60 cm). Initially the column was eluted with chloroform followed by 3% methanol in chloroform to get (−)-Matairesinol.

Further elution of the column with 5% Methanol in chloroform yielded (−)-Wikstromol.

Further elution of the column with 7% Methanol in chloroform yielded Dibenzyl butyrolactol.

The yield of Matairesinol is around 1-2%; the yield of (−)-wikstromol is around 10-14%

The yield of Dibenzylbutyrolactol is around 1-2%.

Characterization of Molecules 1, 2 and 3

(−)-Matairesinol

1. Molecular formula: $C_{20}H_{22}O_6$
2. $^1$H-NMR: 2.53 (4H, m), 2.95(2H, br), 3.86(6H, s), 4.2-4.4(2H, m), 5.5(2H,—OH), 6.4-6.8(6H, m)
3. $^{13}$C-NMR: 34.48(C-8), 38.1(C-8'), 40.90(C-7), 46.60(C-7'), 55.74(2-OMe). 71.31(O—CH2), 111.011, 111.53, 114.11, 114.40, 121.21, 121.95, 129.45, 129.70, 144.30, 144.43, 146.58, 146.68(12* Ar—C), 178.94(—CO—)
4. MS: 358($M^+$)
5. IR: cm−1 3560(—OH), 1765(-lactone)
6. $[\alpha]_d = -37.50°$ (−)-Wikstromol 1. Molecular formula: $C_{20}H_{22}O_7$
2. iH-NMR: 2.40-3.20(5H, m), 3.85(6H, d), 3.95(2H, bd) 5.60(2—OH), 6.5-6.8(6H, m)
3. $^{13}$C-NMR: 31.5(C-7), 41.9(C-8), 43.74(C-7'), 55.94(2-OMe), 70.26(—O—CH2), 76.33(08'), 111.55, 112.81, 114.35, 114.56, 116.82, 121.42, 123.12, 126.20, 130.35, 144.27, 144.95, 146.59(12×Ar—C), 178.66(—CO).
4. MS-374($M^+$)
5. $[\alpha]_d = -30.90°$ C.

Dibenzylbutyrolactol

1. Molecular formula: $C_{20}H_{24}O_6$
2. $^1$H NMR: 6.42-6.81(H-2, m), 6.42-6.81(H-5, m), 6.42-6.81(H-6, m), 2.37-2.80(H-7, m), 1.94-2.18(H-8, m), 5.23 (H-9a, m), 6.42-6.81(H-9b, m), 6.42-6.81(H-2', m), 6.42-6.81(H-5', m), 2.37-2.81(H-6', m), 2.37-2.81(H-7'a, m), 1.94-2.18(H-7'b, m), 4.00-4.09(H-8', t), 3.47-3.57(H-9'a, m), 3.76(—OMe, s), 3.83(—OMe, s).
3. MS-360($M^+$)

EXAMPLE-2

In Vitro Cytotoxicity of (−)-Matairesinol Against Human Cancer Cell Lines:

The human cancer cell lines were obtained either from National center for cell science, Pune, India or National Cancer Institute, Frederick, Md., U.S.A. Cells were grown in tissue culture flasks in complete growth medium (RPMI-1640 medium with 2 mM glutamine, 100 μg/ml streptomycin, pH 7.4, sterilized by filtration and supplemented with 10% sterilized fetal calf serum and 100 units/ml penicillin before use) at 37° C. in an atmosphere of 5% CO2 and 90% relative humidity in a carbon dioxide incubator (WTB binder, Germany). The cells at subconfluent stage were harvested from the flask by treatment with trypsin (0.05% trypsin in PBS containing 0.02% EDTA) and suspended in complete growth medium. Cells with cell viability of more than 97% by trypan blue exclusion technique were used for determination of cytotoxicity.

(−)-Matairesinol was dissolved in DMSO (dimethyl sulphoxide) to obtain a stock solution of 20 mg/ml. The stock solution was serially diluted with complete growth medium containing 50 μg/ml of gentamycin to obtain three working test solutions of 200, 60 and 20 μg/ml The suspension of human cancer cell lines of required cell density in complete growth medium was prepared and cell suspension (1001 μl per wall) of each cell line) of 96-well tissue culture plate. Three additional wells of each cell line were also prepared for control. Two blank wells for control and each experimental and each experimental set for every cell line were also included that contained equivalent amount of complete growth medium only. The plates were incubated at 37° C. in an atmosphere of 5% $CO_2$ and 90% relative humidity in a carbon dioxide incubator.

The working test solutions of (−)-Matairesinol of different concentrations (100 μl) were added after 24-hours incubation in all the wells including blanks of the experimental set. The equivalent amount of complete growth medium was added to control set.

The plates were further incubated for 48-hours (at 37° C. in an atmosphere of 5% $CO_2$ and 90% relative humidity in a carbon dioxide incubator) after addition of test material etc. and then the cell growth was stopped by gently layering of 50 μl of TCA (50% trichloroacetic acid) on top of the medium in all the wells. The plates were incubated at 4° C. for one hour to fix the cells attached to the bottom of the wells. Liquids of all the wells were gently pipetted out and discarded. The plates were washed five times with distilled water to remove TCA, growth medium, low molecular weight metabolites, serum proteins etc. Plates were air-dried.

Cell growth was measured by staining with sulforhodamine B dye (SRB). The SRB solution (100 μl of 0.4% in 1% acetic acid) was added to each well and the plates were incubated at room temperature for 30 minutes. The unbound SRB was quickly removed by washing the wells five times with 1-% acetic acid and plates were air-dried. Tris-buffer (100 μl of 0.01 M, pH 10.4) was added to all the wells and plates were gently stirred for 5 minutes on a mechanical stirrer. The optical density was recorded on ELISA reader at 540 run.

The cell growth in presence of test material was determined by subtracting mean OD value of respective blank from the mean OD value of experimental set. Like wise, cell growth in absence of test material (control set) and in presence of positive control was also determined. The percent cell growth in presence of test material was determined considering the cell growth in absence of test material as 100% and in turn percent inhibition was calculated.

In vitro cytotoxicity of (−)-matairesinol was determined against human breast (MCF-7 & ZR-75-1), neuroblastoma (SK-N-MC & IMR-32), cervix (SiHa), colon (Colo-205, HT-29 & SW-620), liver (HEP-2) and lung (A-549) cancer cell lines. The results are summarized in Table-1. (−)-Matairesinol showed dose dependent inhibition of cell growth of the human cancer cell lines studied. The inhibition varied from 54-93% at 100 μg/ml. It was most effective against human colon cancer cell line Colo-205 and least effective against breast cell line MCF-7.

EXAMPLE-3

In Vitro Cytotoxicity of (−)-Wikstromol Against Human Cancer Cell Lines:

The human cancer cell lines grown and harvested and cytotoxicity was determined exactly as per example 1 except that the test material used was (−)-wikstromol which was dissolved in DMSO and three working test solutions were prepared of the same concentrations as in example 1.

In vitro cytotoxicity of (−)-wikstromol was determined against human breast (MCF-7 & ZR-75-1), neuroblastoma (SK-N-MC & IMR-32), cervix (SiHa), colon (Colo-205, HT-29 & SW-620), liver (HEP-2) and lung (A-549) cancer cell lines. The results are summarized in Table-1. (−)-wikstromol showed dose dependent inhibition of cell growth of the human cancer cell lines studied. The inhibition varied from 32-67% at 100 ug/ml. It was most effective against human colon cancer cell line Colo-205 and least effective against colon cell line HT-29.

EXAMPLE-4

A process for the isolation of novel chemical composition containing lignan mixture from *Cedrus Deodara*.

The dried wood powder of *Cedus deodara* was loaded (200 g.) in a soxhlet apparatus. The powder was first extracted with hexane and followed by chloroform. The chloroform extract concentrated under vacuum. The thick syrupy residue was dissolved in ethylacetate (for about 50 g. of residue around 60 ml. of ethyl acetate). The solution of residue in ethyl acetate was added drop wise to hexane (around 5L.). The solid separated was filtered off.

Yield of Lignan Mixture is Around 20 g.

The composition of lignan mixture was assayed by HPLC for three batches and the results are summarized in Table-2. Column used for HPLC is ODS, 1 0.5 ml flow rate at 225 nm wavelength.

EXAMPLE-5

In Vitro Cytotoxicity of Lignan Mixtures Isolated From *Cedrus deodara* Against Human Cancer Cell Lines:

The human cancer cell lines grown and harvested and cytotoxicity was determined exactly as per example 1 except that the test material used was three lignan mixtures isolated from *Cedrus deodara*, which were dissolved in separately in DMSO and three working test solutions were prepared of the same concentrations as in example 1.

In vitro cytotoxicity of the three lignan mixtures obtained from three batches whose compositions are shown in Table-2 was determined against breast (MCF-7 & T-47-D), cervix (Hela & SiHa), neuroblastoma (SF-539, SK-N-MC, IMR-32, SK-N-SH & SNB-78), colon (Colo-205, HCT-15, HT-29 & SW-620), liver (HEP-2 & HEP-G-2), lung (A-549, HOP-18 & NC1-H23), oral (KB), ovary (NIH-OVCAR-3, OVCAR-5 & SK-OV-3) and prostate (DU-145 & PC-3). The results are summarized in Table-3. Lignan mixture showed dose dependent inhibition of cell growth of the human cancer cell lines studied. All the three mixtures showed more or less the similar pattern of activity. The inhibition varied from 37 to 100% at 100 µg/ml. All the three mixtures were most effective against human oral cancer cell line KB and showed considerably high inhibition towards cervix (SiHa), neuroblastoma (SK-N-MC), colon (Colo-205, HCT-15, HT-29 & SW-620), ovary (OVCAR-5) and prostate (PC-3) cell lines. All the colon cell lines used were found to be highly sensitive to lignan mixtures and there may be tissue specificity for colon. The maximum effect towards liver Hep-G-2, lung HOP-18 and ovary NIH-OVCAR-3 cell lines was observed.

Advantages of the Present Invention.

1. The lignan mixture obtained from *cedrus deodra* is showing anti cancer activity against quite number of cell lines.
2. The lignan mixture exhibiting enhanced anti cancer activity compared to the individual components if used alone.

TABLE 1

In vitro cytotoxicity of (−)-Matairesional and Wikstromol against human cancer cell lines.

| | | Percent growth inhibition | | | | | |
|---|---|---|---|---|---|---|---|
| | | (−)-Matairesional (µg/ml) | | | (−)-Wikstromol (µg/ml) | | |
| | | 10 | 30 | 100 | 10 | 30 | 100 |
| Breast | MCF-7 | 10 | 36 | 54 | 7 | 26 | 51 |
| Breast | ZR-75-1 | | | 62 | | | 37 |
| Neuroblastoma | SKNMC | | | 75 | | | 44 |
| Neuroblastoma | IMR-32 | | | 77 | | | 56 |
| Cervix | SiHa | 10 | 29 | 63 | 16 | 21 | 37 |
| Colon | Colo-205 | 15 | 28 | 93 | 5 | 27 | 67 |
| Colon | HT-29 | | 10 | 74 | | 6 | 32 |
| Colon | SW-620 | | 11 | 68 | 14 | 20 | 50 |
| Liver | Hep-2 | | | 64 | | | 46 |
| Lung | A-549 | 19 | 33 | 65 | 21 | 37 | 56 |

TABLE 2

HPLC assay of three batches of lignan mixtures

| | Relative percentage as assayed by HPLC | | | |
|---|---|---|---|---|
| | (−)-Matairesional | (−)-Wikstromol | Dibenzyl-butyrolactol | Unidentified matter |
| Mixture-1 | 12.20 | 77.30 | 7.70 | 2.80 |
| Mixture-2 | 10.50 | 76.30 | 10.27 | 3.00 |
| Mixture-3 | 10.90 | 78.20 | 8.30 | 2.60 |

TABLE 3

In-vitro cytotoxicity of lignan mixtures isolated from *Cedrus deodara* against human cancer cell lines.

| | | Percent growth inhibition | | | | | | | | |
|---|---|---|---|---|---|---|---|---|---|---|
| | | Mixture - 1 (µg/ml) | | | Mixture - 2 (µg/ml) | | | Mixture - 3 (µg/ml) | | |
| Tissue | Cell line | 10 | 30 | 100 | 10 | 30 | 100 | 10 | 30 | 100 |
| Breast | MCF-7 | 39 | 63 | 72 | 53 | 63 | 66 | 38 | 65 | 71 |
| Breast | T-47-D | 43 | 71 | 80 | 57 | 76 | 77 | 43 | 70 | 75 |

TABLE 3-continued

In-vitro cytotoxicity of lignan mixtures isolated from *Cedrus deodara* against human cancer cell lines.

| | | Percent growth inhibition | | | | | | | | |
|---|---|---|---|---|---|---|---|---|---|---|
| | | Mixture - 1 (μg/ml) | | | Mixture - 2 (μg/ml) | | | Mixture - 3 (μg/ml) | | |
| Tissue | Cell line | 10 | 30 | 100 | 10 | 30 | 100 | 10 | 30 | 100 |
| Cervix | Hela | 11 | 64 | 65 | 23 | 69 | 69 | 20 | 71 | 73 |
| Cervix | SiHa | 38 | 69 | 89 | 67 | 85 | 88 | 44 | 70 | 89 |
| Neuroblastoma | SF-539 | 23 | 72 | 81 | 37 | 76 | 83 | 10 | 71 | 84 |
| Neuroblastoma | SKNMC | 71 | 90 | 91 | 83 | 90 | 90 | 77 | 90 | 92 |
| Neuroblastoma | IMR-32 | — | — | 86 | — | — | 96 | — | — | 89 |
| Neuroblastoma | SKNSH | 9 | 62 | 78 | 10 | 65 | 79 | 14 | 72 | 87 |
| Neuroblastoma | SNB-78 | 26 | 58 | 70 | 46 | 59 | 80 | 28 | 54 | 70 |
| Colon | COLO-205 | 40 | 85 | 95 | 83 | 94 | 98 | 38 | 85 | 94 |
| Colon | HCT-15 | 24 | 73 | 89 | 45 | 89 | 93 | 21 | 75 | 97 |
| Colon | HT-29 | 33 | 76 | 88 | 75 | 85 | 93 | 21 | 78 | 93 |
| Colon | SW-620 | 12 | 54 | 89 | 8 | 62 | 89 | 14 | 62 | 95 |
| Liver | Hep-2 | — | — | 70 | — | — | 73 | — | — | 71 |
| Liver | Hep-G-2 | 14 | 18 | 37 | 11 | 23 | 51 | 19 | 23 | 59 |
| Lung | A-549 | 31 | 63 | 83 | 37 | 80 | 82 | 32 | 67 | 83 |
| Lung | HOP-18 | 2 | 18 | 47 | 9 | 51 | 65 | 0 | 21 | 44 |
| Lung | NCI-H23 | 35 | 88 | 76 | 57 | 72 | 95 | 28 | 74 | 92 |
| Oral | KB | 41 | 87 | 100 | 43 | 87 | 99 | 51 | 85 | 99 |
| Ovary | NIH-OVCAR-3 | 6 | 38 | 44 | 36 | 42 | 48 | 13 | 42 | 37 |
| Ovary | OVCAR-5 | 7 | 44 | 83 | 14 | 76 | 93 | 5 | 50 | 96 |
| Ovary | SK-OV-3 | 6 | 48 | 70 | 17 | 64 | 83 | 2 | 51 | 79 |
| Prostate | DU-145 | 9 | 63 | 81 | 17 | 73 | 81 | 7 | 69 | 82 |
| Prostate | PC-3 | 45 | 91 | 93 | 77 | 92 | 96 | 53 | 94 | 98 |

We claim:

1. A method of treating a patient with cancer comprising: administering a pharmaceutically effective dosage of Matairesinol or a composition containing Matairesinol to said patient, wherein the Matairesinol consists of (−)-Matairesinol.

2. The method as claimed in claim 1, wherein the dosage of (−)-Matairesinol or composition containing (−)-Matairesinol inhibits the growth of cancer cells selected from the group consisting of breast cells, cervix cells, neuroblastoma cells, colon cells, liver cells, and lung cells up to 62%, 63%, 77%, 93%, 65%, and 65% respectively.

3. The method as claimed in claim 2, wherein the cancer cells comprise breast cancer cell MCF-7, breast cancer cell ZR-75-1, cervix cancer cell SiHa, neuroblastoma cancer cell SKNMC, neuroblastoma cancer cells TMR-32, colon cancer cell Colo-205, colon cancer cell HT-29, colon cancer cell SW-620, liver cancer cell Hep-2, or lung cancer cell A-549.

4. The method as claimed in claim 1 comprising administering (−)-Matairesinol singly or in combination with pharmaceutically acceptable carriers.

5. The method as claimed in claim 1 comprising administering (−)-Matairesinol systemically or orally.

6. The method as claimed in claim 1 wherein the patient is an animal.

7. The method as claimed in claim 1 comprising administering the (−)-Matairesinol composition to the patient in combination with a pharmaceutically acceptable carrier, additive, diluent, solvent, filter, lubricant, excipient, binder, stabilizer, or mixture thereof.

8. The method as claimed in claim 1, wherein th cancer is breast cancer, cervical cancer, neuroblastoma, colon cancer, liver cancer, or lung cancer.

9. The method as claimed in claim 1, comprising inhibiting the growth of breast cancer cells by up to 62%, cervical cancer cells by up to 63%, neuroblastoma cells by up to 77%, colon cancer cells by up to 93%, liver cancer cells by up to 65%, lung cancer cells by up to 65%, or a combination thereof.

10. The method as claimed in claim 6, wherein the patient is a mammal.

11. The method as claimed in claim 6, wherein the patient is a human.

12. A method of treating a patient with cancer comprising: administering a pharmaceutically effective dosage of (−)-Matairesinol or a composition containing (−)-Matairesinol to a patient.

13. The method as claimed in claim 12, comprising inhibiting the growth of breast cancer cells by up to 62%, cervical cancer cells by up to 63%, neuroblastoma cells by up to 77%, colon cancer cells by up to 93%, liver cancer cells by up to 65%, lung cancer cells by up to 65%, or a combination thereof.

14. The method as claimed in claim 12 comprising administering (−)-Matairesinol singly or in combination with pharmaceutically acceptable carriers.

15. The method as claimed in claim 12 comprising administering (−)-Matairesinol systemically or orally.

16. The method as claimed in claim 12, wherein the patient is a human.

17. The method of claim 12, wherein the (−)-Matairesinol is pure (−)-Matairesinol.

* * * * *